(12) United States Patent
Uusimaa et al.

(10) Patent No.: US 11,123,137 B2
(45) Date of Patent: Sep. 21, 2021

(54) METHOD AND SYSTEM FOR OPERATING BIOMEDICAL LASER

(71) Applicant: Modulight Oy, Tampere (FI)

(72) Inventors: Petteri Uusimaa, Tampere (FI); Seppo Orsila, Ylöjärvi (FI)

(73) Assignee: Modulight Oy, Tampere (FI)

( * ) Notice: Subject to any disclaimer, the term of this patent is extended or adjusted under 35 U.S.C. 154(b) by 207 days.

(21) Appl. No.: 15/877,445

(22) Filed: Jan. 23, 2018

(65) Prior Publication Data

US 2019/0223953 A1    Jul. 25, 2019

(51) Int. Cl.
*A61B 18/20*       (2006.01)
*A61N 5/06*        (2006.01)
*A61N 5/067*       (2006.01)

(52) U.S. Cl.
CPC ............ *A61B 18/203* (2013.01); *A61B 18/20* (2013.01); *A61N 5/06* (2013.01); *A61N 5/062* (2013.01); *A61N 5/0616* (2013.01); *A61N 2005/067* (2013.01)

(58) Field of Classification Search
CPC .. A61B 18/203; A61B 18/20; A61N 2005/067
See application file for complete search history.

(56) References Cited

U.S. PATENT DOCUMENTS

| | | | | |
|---|---|---|---|---|
| 2002/0022920 A1* | 2/2002 | Straub | ................ | B60K 31/0058 701/93 |
| 2005/0154380 A1* | 7/2005 | DeBenedictis | ...... | A61B 18/203 606/9 |
| 2006/0129140 A1* | 6/2006 | Todd | .................... | G06Q 10/087 606/1 |
| 2009/0248448 A1 | 10/2009 | Zakay et al. | | |
| 2013/0281991 A1* | 10/2013 | Mosedale | ........... | A61F 9/00825 606/4 |
| 2016/0321422 A1* | 11/2016 | Albright | ............... | A61N 5/0616 |
| 2017/0319285 A1* | 11/2017 | Shibazaki | ................ | B25J 9/163 |
| 2017/0329903 A1* | 11/2017 | Shu | .................... | G06F 16/24553 |
| 2018/0130551 A1* | 5/2018 | Gass et al. | ............. | G61H 29/17 |

FOREIGN PATENT DOCUMENTS

WO    2014/060874 A1    4/2014

OTHER PUBLICATIONS

International Search Report and Written Opinion received for International Patent Application No. PCT/FI2019/050015, dated Feb. 26, 2019, 16 pages.

* cited by examiner

*Primary Examiner* — Gary Jackson
*Assistant Examiner* — Zahed Kabir
(74) *Attorney, Agent, or Firm* — Ziegler IP Law Group, LLC (57) ABSTRACT

A method for operating a biomedical laser. The method includes providing the biomedical laser having a first range of operational parameters; providing a second range of operational parameters for the biomedical laser; activating the biomedical laser to operate within the second range of operational parameters; identifying a need for a change in operational parameters of the biomedical laser; and triggering an action based on the identified need. The action includes providing a third range of operational parameters for the biomedical laser and activating the biomedical laser to operate within the third range of operational parameters; and de-activating a range of operational parameters. The second and third range of operational parameters is within the first range of operational parameters.

14 Claims, 2 Drawing Sheets

FIG. 3

METHOD AND SYSTEM FOR OPERATING BIOMEDICAL LASER

TECHNICAL FIELD

The present disclosure relates generally to use of lasers for biomedical applications; and more specifically, to methods for operating biomedical lasers. Furthermore, the present disclosure also relates to systems for operating aforementioned biomedical lasers.

BACKGROUND

Nowadays, lasers are increasingly being used for several biomedical applications. Though prevalent in ophthalmology and dermatology, lasers have also found use in surgical procedures, cancer diagnosis and treatment, biomedical imaging, gene sequencing and the like. Therefore, in many biomedical applications, lasers have become a mainstay and are quickly replacing conventional tools. Often, a laser is configured to emit light of a wavelength that matches absorption lines of a certain type of body tissue or chemical compound like drug or organic molecule like base in DNA, thereby triggering a specific biochemical or biomechanical process in the target. For example, a certain wavelength of light affects only the matching body tissue while having no effect on other body tissues. For example, a carbon dioxide gas laser can be used for laser surgery on soft tissue, whereas dye laser is best suited for dermatological applications since wavelength of the dye laser matches absorption lines of tissues including melanin or hemoglobin.

Typically, a biomedical laser comes with a wide range of operational parameters. However, a specific range of operational parameters is selected, and the biomedical laser is configured with such selected range to be suitably operable for a specific treatment modality. In such instance, the wide range of operational parameters of the biomedical laser is not utilized fully. Also, the biomedical lasers are typically associated with various usage limitations mostly based on approval of such usage. This also leads to a situation where the biomedical laser is not utilized fully. Accordingly, when there is a need for operating the same biomedical laser based on various treatment modalities, operational parameters and/or usage limitations, the biomedical laser may not be operated or used efficiently based on such needs.

Therefore, in light of the foregoing discussion, there exists a need to overcome the aforementioned drawbacks associated with the operation of a biomedical laser.

SUMMARY

The present disclosure seeks to provide a method for operating a biomedical laser. The present disclosure also seeks to provide a system for operating a biomedical laser. The present disclosure seeks to provide a solution to the existing problems of limited operation or usage of a biomedical laser. An aim of the present disclosure is to provide a solution that overcomes at least partially the problems encountered in prior art, and provides a wide range of operations or usage of a biomedical laser based on a need.

In one aspect, an embodiment of the present disclosure provides a method for operating a biomedical laser, the method comprising:

providing the biomedical laser having a first range of operational parameters;

providing a second range of operational parameters for the biomedical laser, wherein the second range of operational parameters is within the first range of operational parameters;

activating the biomedical laser to operate within the second range of operational parameters;

identifying a need for a change in operational parameters of the biomedical laser; and triggering an action based on the identified need, wherein the action comprises at least one of:

providing a third range of operational parameters for the biomedical laser, wherein the third range of operation parameters is within the first range of operational parameters; and activating the biomedical laser to operate within the third range of operational parameters; and de-activating a range of operational parameters.

In another aspect, an embodiment of the present disclosure provides a system for operating a biomedical laser, the biomedical laser having a first range of operational parameters, the system comprising:

a processor coupled to the biomedical laser, the processor being configured to provide a second range of operational parameters for the biomedical laser, wherein the second range of operational parameters is within the first range of operational parameters;

activate the biomedical laser to operate within the second range of operational parameters;

identify a need for a change in operational parameters of the biomedical laser; and trigger an action based on the identified need, wherein the action comprises at least one of:

providing a third range of operational parameters for the biomedical laser, wherein the third range of operational parameters is within the first range of operational parameters; and activating the biomedical laser to operate within the third range of operational parameters;

de-activating a range of operational parameters.

Embodiments of the present disclosure substantially eliminate or at least partially address the aforementioned problems in the prior art, and enables a need based operation for a biomedical laser.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a method for operating a biomedical laser, the method comprising:

providing the biomedical laser having a first range of operational parameters;

providing a second range of operational parameters for the biomedical laser, wherein the second range of operational parameters is within the first range of operational parameters;

activating the biomedical laser to operate within the second range of operational parameters;

identifying a need for a change in operational parameters of the biomedical laser; and triggering an action based on the identified need, wherein the action comprises at least one of:

providing a third range of operational parameters for the biomedical laser, wherein the third range of operational parameters is within the first range of operational parameters; and activating the biomedical laser to operate within the third range of operational parameters; and de-activating a range of operational parameters.

In another aspect, an embodiment of the present disclosure provides a system for operating a biomedical laser, the biomedical laser having a first range of operational parameters, the system comprising:

a processor coupled to the biomedical laser, the processor being configured to provide a second range of operational parameters for the biomedical laser, wherein the second range of operational parameters is within the first range of operational parameters;

activate the biomedical laser to operate within the second range of operational parameters;

identify a need for a change in operational parameters of the biomedical laser; and trigger an action based on the identified need, wherein the action comprises at least one of:

providing a third range of operational parameters for the biomedical laser, wherein the third range of operational parameters is within the first range of operational parameters; and activating the biomedical laser to operate within the third range of operational parameters;

de-activating a range of operational parameters.

The present disclosure provides the aforementioned method and system for operating the biomedical laser. The disclosed method and system provides a biomedical laser that is operable with a wide range of treatment modalities or treatment parameters. The treatment modalities or treatment parameters are operable to change based on an identified need. In this way various operational parameters of the biomedical laser are made fully utilizable and operable for different treatments. Additionally, based on the need and the approval of usage, the same biomedical laser may be operated or used efficiently based on the need associated with various treatment modalities. Further beneficially, after suitable configuration depending on certain treatment modality, such biomedical laser may be operated by a user with moderate technical proficiency.

Throughout the present disclosure, the term 'biomedical laser' relates to a device (or an equipment) employing use of a laser light emitter to generate light for purpose of biomedical applications (namely biomedical diagnosis and biomedical procedures). Examples of such biomedical applications include, but are not limited to, cosmetic procedures, surgical procedures, biomedical imaging or illumination, drug activation, and dental or ophthalmic treatments. Therefore, the biomedical laser is required to be configured differently for different biomedical applications.

As mentioned previously, the provided biomedical laser includes a first range of operational parameters. Throughout the present disclosure, the term 'first range of operational parameters' relates to a wide range of operational parameters associated with the biomedical laser. For example, the 'first range of operational parameters' may be a pre-configured range of operational parameters defining an overall range (i.e. minimum to maximum ranges for operational parameters) of the biomedical laser.

According to an embodiment, the first range of operational parameters may be associated with at least one of a target wavelength of the biomedical laser, a target energy output of the biomedical laser and an operational mode selected from a group of a treatment modality, biomedical activation and measurement process of the biomedical laser. Optionally, the first range of operational parameters is further associated with at least one of current input for operation of the biomedical laser, voltage input for operation of the biomedical laser and operating temperature of the biomedical laser.

As mentioned previously, a second range of operational parameters is provided for the biomedical laser, and the second range of operational parameters is within the first range of operational parameters. The term 'second range of operational parameters' used herein relates to a selected range of operational parameters, from within the first range of operational parameters, and may be associated with a specific treatment modality.

According to an embodiment, the biomedical laser may be configured for plurality of biomedical applications based on a selected range of operational parameters (such as the second range of operational parameters). Therefore, the biomedical laser is associated with a plurality of treatment modalities. Throughout the present disclosure, the term 'treatment modality of the biomedical laser' relates to at least one mode (or at least one manner) of operation of the biomedical laser, wherein such at least one mode of operation depends on the at least one range of operational parameters (such as the second range of operational parameters). Therefore, a treatment modality of the biomedical laser is associated with at least one of the target wavelength of the biomedical laser, the target energy output of the biomedical laser, the current input for operation of the biomedical laser, the voltage input for operation of the biomedical laser and the operation temperature of the biomedical laser.

According to an embodiment, the selection of the second range of operational parameters may be associated with configuration of the biomedical laser for a biomedical application such as photodynamic therapy, as photocoagulation and so forth.

The biomedical laser is activated to operate within the second range of operational parameters. Optionally, the second rage of operational parameters is provided by a trained biomedical practitioner. In this regard, the trained biomedical practitioner may input the second range of operational parameters (i.e. select the second range of operational parameters from within the first range of operational parameters) on a computing device including the processor coupled to the biomedical laser.

Optionally, activating the biomedical laser to operate with the second range of operational parameters includes controlling operation of a laser light emitter of the biomedical laser by the processor. The processor may control operation of the laser light emitter to emit light in accordance with the second range of operational parameters. For example, the processor provides the current input and the voltage input and the temperature input to the laser light emitter for operation of the biomedical laser.

Optionally, the laser light emitter comprises at least one light emitting element, such as a light emitting circuit, and the processor is configured to control the at least one light emitting element to emit light of at least one target wavelength. As an example, the laser light emitter of the biomedical laser may be operated to emit monochromatic light (upon activation of the biomedical laser with the second range of operational parameters) at a target wavelength of 632 nanometer (nm) for activating a specific drug or dye molecule in photodynamic therapy application. Similarly, the same laser light emitter of the biomedical laser may be operated to emit monochromatic light at a target wavelength of 635 nm for activating another drug or dye molecule in photodynamic therapy.

Optionally, the biomedical laser comprises a plurality of light emitting circuits. The light emitting circuits may be operated to emit monochromatic light with same or different target wavelengths. The circuits might be independently operated from each other. For example, a first light emitting circuit might emit a target wavelength of 532 nm and a second might emit another target wavelength of 660 nm. Further, the target wavelength of 532 nm may enable activating a fluorescent dye in a gene sequencing application, whereas the target wavelength of 660 nm may enable activating another set of fluorescent dyes in a gene sequencing application. Moreover, the second light emitting circuit may be remotely activated for use at a later period of time. As another example, the first light emitting circuit may provide light continuously and the second may provide in a pulsed manner during a treatment modality.

As mentioned previously, the method comprises identifying a need for a change in operational parameters of the biomedical laser. The term 'need' used herein relates to a change required with respect to the configuration of the biomedical laser and operational parameters thereof for suitable operation of the same biomedical laser for different biomedical applications or in different conductions, which will be explained in greater detail herein later.

According to an embodiment, the need is typically associated with the use of the same biomedical laser for different biomedical applications. Optionally, the need may be associated with change in location of the biomedical laser, change in user, change in accessories used along with the biomedical laser, and usage limitations, which are explained in greater detail herein later.

As mentioned previously, the method comprises triggering an action based on the identified need. The action comprises at least one of providing a third range of operational parameters for the biomedical laser, wherein the third range of operational parameters is within the first range of operational parameters, and activating the biomedical laser to operate within the third range of operational parameters; and de-activating a range of operational parameters.

According to an embodiment, the term 'third range of operational parameters' used herein includes a range of operational parameters essentially different from the second range of operational parameters but within the first range of operational parameters. Optionally, the second and third ranges of operational parameters may have an overlap therebetween.

The biomedical laser is activated to operate within the third range of operational parameters based on the need. For example, the biomedical laser may be configured with the third range of operational parameters and activated to meet the need, for example, to perform a specific biomedical application associated with a specific treatment modality. It may be appreciated that such biomedical application or treatment modality may be different from the biomedical application or treatment modality attained when the biomedical laser is activated to operate within the second range of operational parameters. For example, the second range of operational parameters may activate the biomedical laser to operate with the target wavelength of 532 nm that may enable activating a fluorescent dye in a gene sequencing application, whereas the third range of operational parameters may activate the biomedical laser to operate with the target wavelength of 660 nm that may enable activating another set of fluorescent dyes in a gene sequencing application. In such instance, the need for a change in operational parameters of the biomedical laser is based on the need for change in the target wavelength (i.e. operational parameters), i.e. from the target wavelength of 532 nm to 660 nm. Therefore, the need for change in the operational parameters may be associated with the need for change in the biomedical applications or treatment modalities to be performed by the biomedical laser.

According to an embodiment, the term 'de-activating a range of operational parameters' used herein refers to de-activating other ranges of operational parameters other than the third range of operational parameters. For example, if the biomedical laser may be configured to have ten ranges of operational parameters, and when based on the identified need the third range of operational parameters is provided for the operation of the biomedical laser, the remaining nine ranges (i.e. the first and second, and fourth to tenth ranges of operational parameters) are de-activated.

In one embodiment, identifying the need for the change in operational parameters of the biomedical laser comprises measuring an operational response of the biomedical laser whilst the biomedical laser is operated using the second range of operational parameters; and comparing the measured operational response with treatment modality parameters of a first treatment.

Optionally, the term 'operational response' of the biomedical laser relates to variation of operational characteristics of the biomedical laser, whilst the biomedical laser is operated using the second range of operational parameters. For example, measuring the operational response of the biomedical laser comprises measuring at least one of voltage transient as a function of time, current transient as a function of time, temperature of the laser light emitter, power usage of the biomedical laser during operation, and so forth. Furthermore, it will be appreciated that operational response parameters are measured by employing measuring instruments such as voltage meters, current meters, thermometers, and the like. As an example, the voltage transient (namely voltage fluctuations within the laser light emitter) and the current transient (namely current fluctuations within the laser light emitter) may be measured as a function of time, to constitute measured operational response of the biomedical laser. In such an example, the processor coupled to the biomedical laser may record variation of the current input and the voltage input with regard to time to detect and measure the current and voltage transients respectively.

According to an embodiment, the measured operational response is compared with the treatment modality parameters of the first treatment. It may be appreciated that the treatment modality parameters is associated with the ranges of operational parameters of the biomedical laser. In the present embodiment, the treatment modality parameters of the first treatment corresponds to the third range of operational parameters for the biomedical laser, which in turn corresponds to the action triggered based on the identified need. Therefore, the need for the change in the second range of operational parameters of the biomedical laser is to identify the third range of operational parameters for the biomedical laser, which allows the biomedical laser to perform the first treatment confirming the treatment modality parameters.

According to an embodiment, the measured operational response (of the biomedical laser while operated using the second range of operational parameters) is compared with treatment modality parameters of the first treatment to identify and validate whether the third range of operational parameters is suitable or not for the first treatment. Therefore, upon finding match between the measured operational response (of the biomedical laser while operated using the second range of operational parameters) and treatment modality parameters of the first treatment the biomedical laser is activated to operate within the third range of operational parameters. Moreover, based on the need for the first treatment, the second range of operational parameters for the biomedical laser is changed to the third range of operational parameters.

Optionally, identifying the need for the change in operational parameters of the biomedical laser comprises comparing the treatment modality parameters of the first treatment with the first range of operational parameters. It will be appreciated that the treatment modality parameters, which correspond to operational parameters of the biomedical laser, will be within the first range of operational parameters, i.e. the wide range of the operational parameters.

According to another embodiment, if there is need for treatment modality parameters for a second treatment, measured operational response of the biomedical laser (whilst the biomedical laser is operated using the third range of operational parameters) is compared with treatment modality parameters of the second treatment. Accordingly, upon finding match between the measured operational response (of the biomedical laser while operated using the third range of operational parameters) and treatment modality parameters of the second treatment the biomedical laser is activated to operate within a fourth range of operational parameters. It will be appreciated that the fourth range of operational parameters is essentially different from the second and third ranges of operational parameters but within the first range of operational parameters. Optionally, the second, third and fourth ranges of operational parameters may have an overlap therebetween.

Optionally, identifying the need for the change in operational parameters of the biomedical laser comprises detecting change in location of the biomedical laser. It will be appreciated that identification of the need for the change in operational parameters of the biomedical laser is based on detection of change in location of the biomedical laser. For example, the need may be location specific, i.e. a biomedical laser may be required to be configured in a particular manner with respect to usages thereof in one location (which may be a country) and same biomedical laser may be required to be configured in another manner with respect to usages thereof in another location (which may be another country). Accordingly, the operational parameters of the biomedical laser may be changed based on the need of change in the locations.

Optionally, identifying the need for the change in operational parameters of the biomedical laser comprises analyzing a user profile of a user using the biomedical laser. It will be appreciated that the user profile of the user may define proficiency to operate the biomedical laser for a particular treatment, or to operate the biomedical laser within a specific range of operational parameters. In such instance, the need is user specific, i.e. a particular user may be proficient to operate the biomedical laser for a particular treatment or within a specific range, whereas a new user may or may not be proficient to operate the biomedical laser for such treatment or within such specific range. Therefore, the proficiency of the new user needs to be checked for suitable and allowable operation of the biomedical laser. Accordingly, the operational parameters of the biomedical laser may be changed based on the need of change in the user profiles.

Optionally, identifying the need for the change in operational parameters of the biomedical laser comprises analyzing accessories used with the biomedical laser. It will be appreciated that the biomedical laser may be used in conjunction with various accessories for making the biomedical laser operable for various treatments or to operate within a specific range of operational parameters. For example, the accessories may include optical lenses or assemblies, a drug or a chemical, or a light delivery system like a scanner or a medical fiber and so forth, and use thereof may generate a need for change in the operational parameters for desired operation of the biomedical laser. Similarly, any change in the accessory associated with the biomedical laser generates a need for change in the operational parameters of the biomedical laser for the desired operation thereof. Accordingly, the operational parameters of the biomedical laser may be changed based on the need of change in the accessories.

According to an embodiment, identifying the need for the change in operational parameters of the biomedical laser comprises obtaining at least one usage limitation parameter. The term 'usage limitation' used herein relates to technical and/or legal regulations governing the operation of the biomedical laser.

Optionally, the at least one usage limitation parameters is selected from a group consisting of: approval related to usage of a certain range of defined treatment modalities or treatment parameters, approval of accessories or drugs or treatment recipes used in connection with the defined treatment modalities, lease/service agreement or access fee related to the biomedical laser, and patent restrictions related to the usage.

According to an embodiment, approval related to usage of the certain range of defined treatment modalities or treatment parameters may be associated with a particular location (or geography), proficiency of a user, accessories used with the biomedical laser, and so forth. For example, a particular location or geography (such as a country) may approve usage of a certain range of defined treatment modalities or treatment parameters, whereas another location or geography (such as another country) may not approve such usage. Similarly, the user proficiency and the accessories used with the biomedical laser may limit the usage of the biomedical laser for certain treatments. These limitations of usage generate a need for change in operational parameters of the biomedical laser for desired operation thereof. Accordingly, the operational parameters of the biomedical laser may be changed based on the need associated with usage of the certain range of defined treatment modalities or treatment parameters.

In one embodiment, approval of accessories or drugs or other chemicals or treatment recipes used in connection with the defined treatment modalities may be associated with acceptance of the accessories or drugs or chemicals or treatment recipes at a target site or for a certain medical treatment modality. Optionally, approval for the accessories or drugs or chemicals or treatment recipes may be obtained using information extracted from a database having a list of approved drugs and accessories associated with the biomedical laser, and thus providing a set of operational parameters based on the approval data. The accessory compatibility includes, but is not restricted to the tested and qualified devices with valid user license used with the biomedical laser.

In one embodiment, the lease/service agreement or access fee related to the biomedical laser is associated with legal and monetary requirements to be fulfilled by a user or an organization for using the biomedical laser. Therefore, the user or organization, fulfilling such legal and monetary requirement, may be allowed to use biomedical laser.

According to an embodiment, the patent restrictions related to the usage are typically associated with a location or geography. For example, patent right enforcement with respect to certain geography may or not allow use of a biomedical laser in such geography.

Optionally, ambient temperature around the biomedical laser can be obtained using a temperature sensor or external source (such as room temperature sensor of office/home automation system). Further, the biomedical laser might have a range of approved ambient temperature ranges. The approved ambient temperature ranges are typically defined in the biomedical laser acceptance specification. The ambient temperature can be used as an additional parameter to determine treatment modalities. As an example, if the ambient temperature is outside of safe operational margin the treatment modalities might be changed to prohibit usage of the biomedical laser totally or for certain treatments. The term 'ambient temperature' can be understood broadly to refer to external or internal temperatures of the biomedical laser.

As mentioned previously, the system comprises a processor coupled to the biomedical laser. It will be appreciated that the system mentioned herein enables in implementing the aforesaid method. Accordingly, the processor is configured to provide a second range of operational parameters for the biomedical laser, wherein the second range of operational parameters is within the first range of operational parameters; activate the biomedical laser to operate within the second range of operational parameters; identify a need for a change in operational parameters of the biomedical laser; and trigger an action based on the identified need, wherein the action comprises one of providing a third range of operational parameters for the biomedical laser, wherein the third range of operation parameters is within the first range of operational parameters; and activating the biomedical laser to operate within the third range of operational parameters; de-activating the biomedical laser to operate within the second range of operational parameters.

Optionally, the system further comprises at least one measuring instrument communicably coupled to the processor. The measuring instrument may include voltage meters, current meters, thermometers, and the like. The at least one measuring instrument is configured to measure an operational response of the biomedical laser whilst the biomedical laser is operated using the second range of operational parameters. It will be appreciated that the operational response are measured by the measuring instruments, and the measured operational response are transmitted to the processor. The processor with the help of the measured operational response may record variation of the current input and the voltage input with regard to time to detect and measure the current and voltage transients, respectively. It may be appreciated that the voltage transient (namely voltage fluctuations within the laser light emitter) and the current transient (namely current fluctuations within the laser light emitter) may be measured as a function of time, to constitute measured operational response of the biomedical laser.

Optionally, the processor is configured to compare the measured operational response with treatment modality parameters of a first treatment to identify the need for the change in operational parameters of the biomedical laser. As mentioned herein above, the processor is operable to compare the measured operational response (of the biomedical laser while operated using the second range of operational parameters) with treatment modality parameters of the first treatment to identify and validate whether the third range of operational parameters is suitable or not for the first treatment. Moreover, upon finding match between the measured operational response and treatment modality parameters of the first treatment, the biomedical laser may be activated to operate within the third range of operational parameters. Similarly, the processor is operable to compare the measured operational response (of the biomedical laser whilst operated using the third range of operational parameters) with treatment modality parameters of a second treatment to identify and validate whether a fourth range of operational parameters is suitable or not for the second treatment.

Optionally, the processor is configured to compare the treatment modality parameters of the first treatment with the first range of operational parameters to identify the need for the change in operational parameters of the biomedical laser.

Optionally, the system comprises a location sensing unit configured to detect a location of the biomedical laser; the location sensing unit is communicably coupled to the processor. The processor is configured to identify the need for the change in operational parameters of the biomedical laser upon detection of change in the location of the biomedical laser. The term 'location sensing unit' used herein relates to a device, chip and the like that is operable to detect a location of the biomedical laser. According to an embodiment, the location sensing unit may include a Global Positioning System (GPS) or wireless fidelity (WIFI) module or similar operable to determine the location of the biomedical laser. The location sensing unit may be arranged inside or outside the biomedical laser. The location sensing unit is operable to determine the location of the biomedical laser and transmit the determined location to the processor. The processor accordingly operable to detect the change in location of the biomedical laser based on received locations. Consequently, the processor is configured to identify a need for the change in operational parameters of the biomedical laser upon detection of change in the location of the biomedical laser. Additionally, the processor may be operable to prompt changes to the operational parameters of the biomedical laser based on the need associated with the change in the locations.

Optionally, the system comprises an identity recognition unit configured to recognizing a user profile of a user using the biomedical laser. The identity recognition unit is communicably coupled to the processor, and the processor is configured to identify the need for the change in operational parameters of the biomedical laser upon analysis of the user profile of the user. Further, the term 'identity recognition unit' used herein relates to an image sensing device, a scanner and so forth, which is operable to recognize an identity of the user using the biomedical laser. In addition, the term 'identity recognition unit' can refer to identifying the user using the biomedical laser by identification card, login credentials (password and user name) or other similar identification method. Furthermore, the identity recognition unit may be arranged on the biomedical laser and/or may be operatively coupled to the processor for recognizing the identity of the user. The processor is operable to detect an identity (associated with a user profile) of the user based on the identity of the user being recognized by the identity recognition unit. In an example, a biomedical laser may be used by a dermatologist, a dental surgeon, and the like, and in such instance, the identity recognition unit detects difference in the identity or user profiles of the users and such different identifications would be communicated to the processor. Consequently, the processor is operable to identify the need for the change in operational parameters of the biomedical laser based upon identification of the user profile of the user using the biomedical laser. Additionally, the processor may be operable to prompt changes to the operational parameters of the biomedical laser based on the need associated with the change in the user profile.

Optionally, the system comprises an accessory recognition unit configured to obtain information pertaining to accessories used with the biomedical laser. The accessory recognition unit is communicably coupled to the processor, and the processor is configured to identify the need for the change in operational parameters of the biomedical laser upon analyzing the obtained information pertaining to the accessories used with the biomedical laser. The term 'accessory recognition unit' used herein relates to an arrangement of electronic elements operable to obtain information pertaining to accessories used with the biomedical laser. It may be appreciated that the accessories used with the biomedical laser may include optical lenses or assemblies, a drug or a chemical, or a light delivery system like a scanner or a medical fiber and so forth. Therefore, the accessory recognition unit is operable to obtain information pertaining to change in the accessories used in conjunction with the biomedical laser. Consequently, the processor is operable to identify the need for the change in operational parameters of the biomedical laser based on the obtained information pertaining to the accessories. Additionally, the processor may be operable to prompt changes to the operational parameters of the biomedical laser based on the need associated with the change in the accessories.

According to an embodiment, the at least one measuring instrument, the location sensing unit, the identity recognition unit, and the accessory recognition unit are communicably coupled to the processor. For example, the at least one measuring instrument, the location sensing unit, the identity recognition unit, and the accessory recognition unit may be communicably coupled, using a wired communication, a wireless communication or a combination thereof, to the processor.

Optionally, the system further comprises a database communicably coupled to the processor. The processor is configured to identify the need for the change in operational parameters of the biomedical laser upon obtaining at least one usage limitation parameter from the database. The database may be a storage device or a directory where informational data related to the usage limitation parameter are stored and can be retrieved. The database is communicably coupled to the processor using a communication network. For example, the communicably network may be wired, wireless or a combination thereof. Examples of the network include, but are not limited to, Local Area Networks (LANs), Wide Area Networks (WANs), radio network, Internet, radio networks, and telecommunication networks.

More optionally, as disclosed herein above, the at least one usage limitation parameters is selected from a group consists of approval related to usage of a certain range of defined treatment modalities or treatment parameters, and approval of accessories or drugs used in connection with the defined treatment modalities, lease/service agreement or access fee related to the biomedical laser, and patent restrictions related to the usage. Additionally the user of the biomedical laser might load from a server system an approved recipe/recipes to a certain modality or treatment to be used/associated with the at least one usage limitation parameter. The approved recipe term refers to medical professional approved setup on how to run possible treatment or how to use the biomedical laser.

DETAILED DESCRIPTION OF THE DRAWINGS

Figure 1:
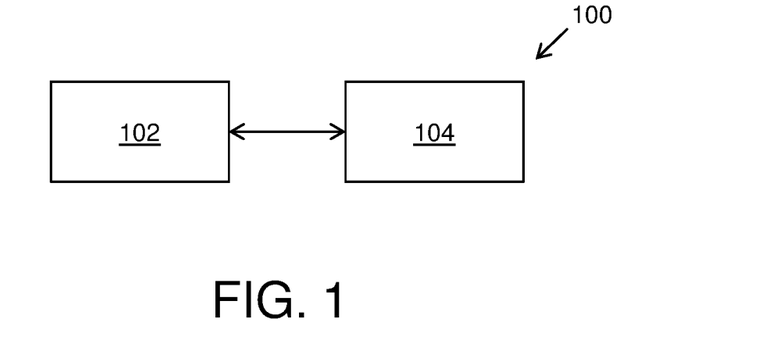
FIGS. 1 and 2 are block diagrams of systems for operating a biomedical laser, in accordance with embodiments of the present disclosure.

Referring to FIG. 1, illustrated is a block diagram of a system 100 for operating a biomedical laser 102, in accordance with an embodiment of the present disclosure. As shown, the system 100 comprises a processor 104 coupled to the biomedical laser 102. The processor 104 is operable to identify a need for a change in operational parameters of the biomedical laser 102 and trigger an action based on the identified need.

Figure 2:
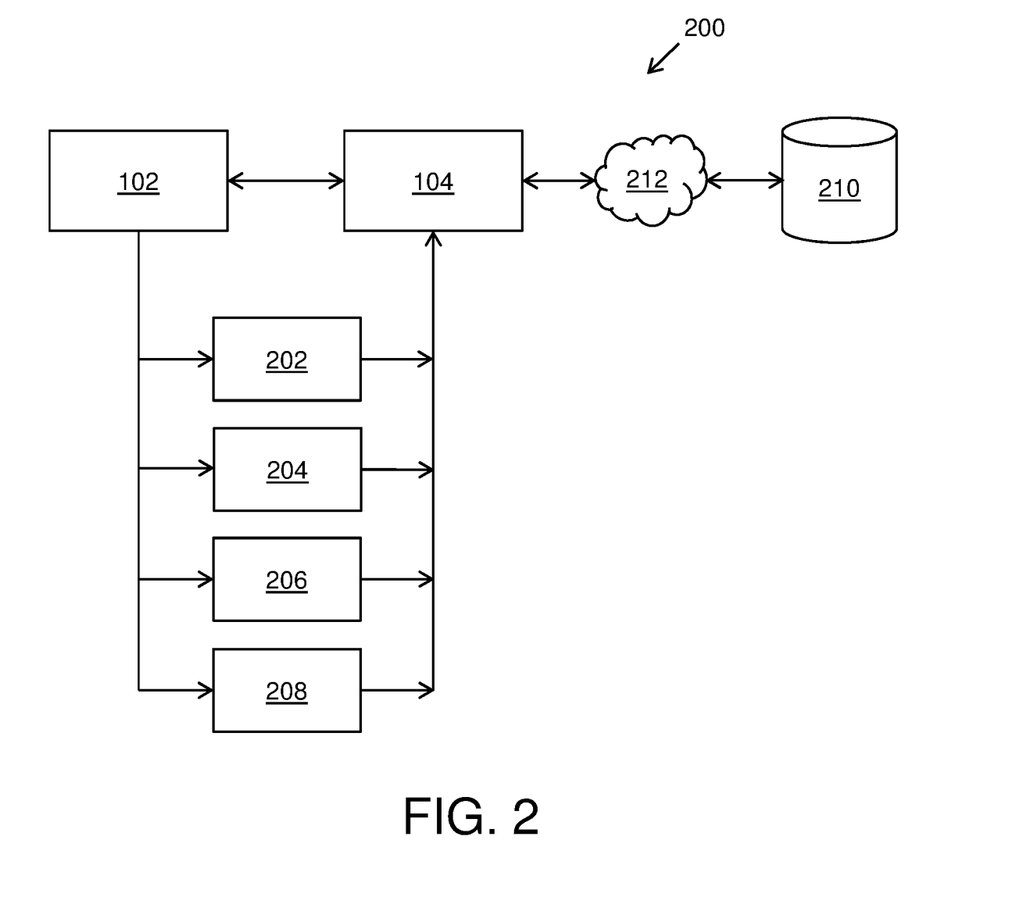

Referring to FIG. 2, there is shown a block diagram of a system 200 for operating a biomedical laser (such as the biomedical laser 102, shown in FIG. 1), in accordance with another embodiment of the present disclosure. The system 100 comprises a processor (such as the processor 104, as shown in FIG. 1) coupled to the biomedical laser 102. The system 200 further comprises at least one measuring instrument 202, a location sensing unit 204, an identity recognition unit 206, and an accessory recognition unit 208 communicably coupled to the processor 104. The system 200 also comprises a database 210 communicably coupled to the processor 104 using a communication network 212.

Figure 3:
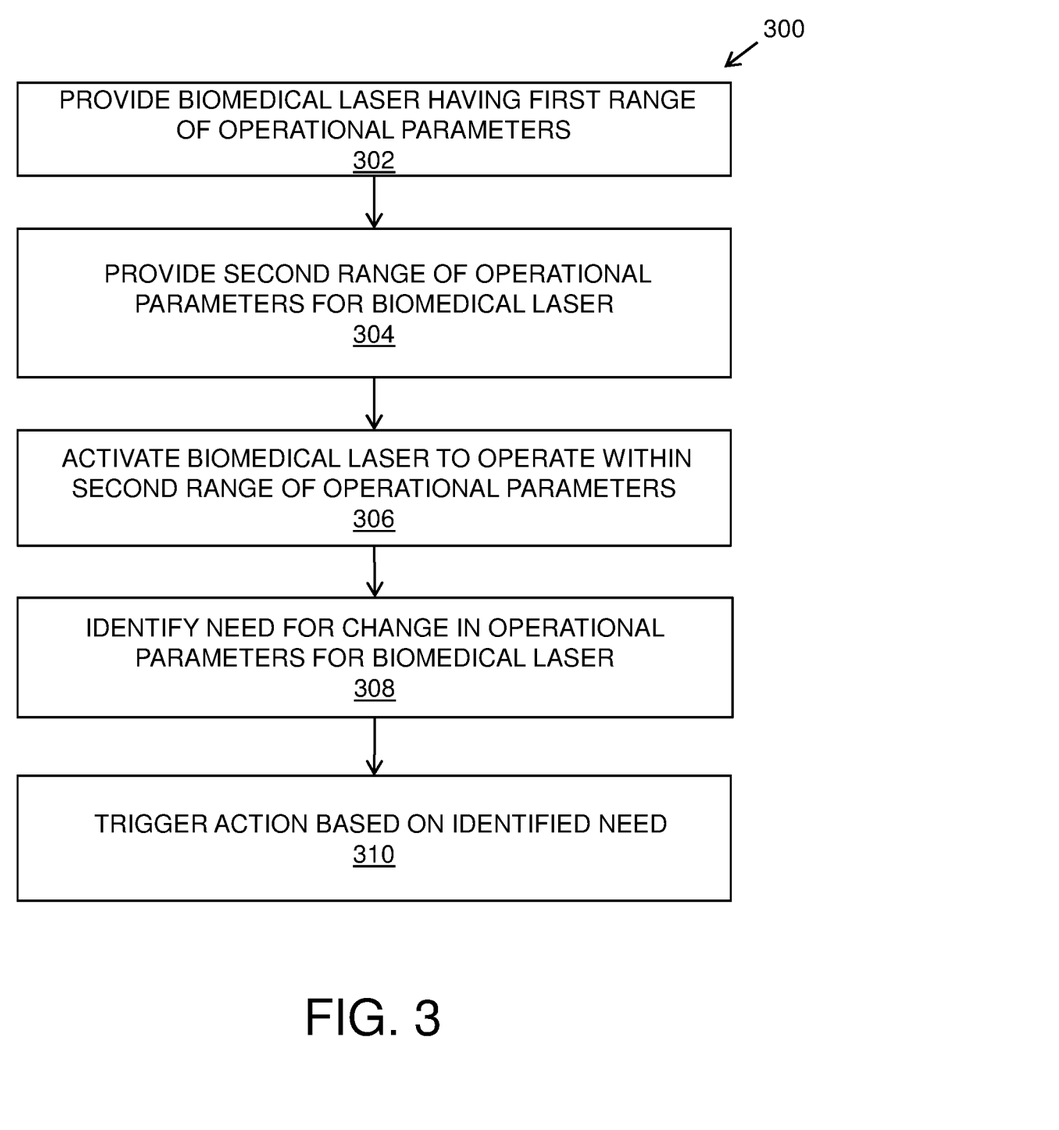
FIG. 3 illustrates steps of a method for operating a biomedical laser, in accordance with an embodiment of the present disclosure.

Referring to FIG. 3, illustrated are steps of a method 300 for operating a biomedical laser (such as the biomedical lasers 100 and 200 of FIGS. 1 and 2), in accordance with an embodiment of the present disclosure. At step 302, the biomedical laser is provided, and the biomedical laser has a first range of operational parameters. At step 304, a second range of operational parameters is provided for the biomedical laser, the second range of operational parameters is within the first range of operational parameters. At step 306, the biomedical laser is activated to operate within the second range of operational parameters. At step 308, a need for a change in operational parameters is identified for the biomedical laser. At step 310, an action is triggered based on the identified need. The action comprises providing a third range of operational parameters for the biomedical laser and activating the biomedical laser to operate within the third range of operational parameters; and de-activating a range of operational parameters. The third range of operation parameters is within the first range of operational parameters.

The steps 302 to 310 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method for operating a biomedical laser, the method comprising:
providing the biomedical laser having a first range of operational parameters;
providing a second range of operational parameters for the biomedical laser, wherein the second range of operational parameters is within the first range of operational parameters;
activating the biomedical laser to operate within the second range of operational parameters;
identifying a need for a change in operational parameters of the biomedical laser comprising detection of a change in geographical location of the biomedical laser and obtaining from a database via a communication network, at least one usage limitation parameter relating to legal regulations governing the operation of the biomedical laser, comprising patent restrictions associated with the geographical location of the biomedical laser that may or may not allow use of the biomedical laser; and
triggering an action based on the identified need, wherein the action comprises:
providing a third range of operational parameters for the biomedical laser from the database via the communication network, wherein the third range of operation parameters is within the first range of operational parameters; and activating the biomedical laser to operate within the third range of operational parameters; and
de-activating a range of operational parameters.

2. A method according to claim 1, wherein identifying the need for the change in operational parameters of the biomedical laser comprises measuring an operational response of the biomedical laser whilst the biomedical laser is operated using the second range of operational parameters; and
comparing the measured operational response with treatment modality parameters of a first treatment.

3. A method according to claim 1, wherein identifying the need for the change in operational parameters of the biomedical laser comprises comparing the treatment modality parameters of the first treatment with the first range of operational parameters.

4. A method according to claim 1, wherein identifying the need for the change in operational parameters of the biomedical laser comprises detecting change in location of the biomedical laser.

5. A method according to claim 1, wherein identifying the need for the change in operational parameters of the biomedical laser comprises analyzing a user profile of a user using the biomedical laser comprising medical certifications or credentials for such user to deliver a treatment with such parameters and settings.

6. A method according to claim 1, wherein identifying the need for the change in operational parameters of the biomedical laser comprises analyzing accessories used with the biomedical laser.

7. A method according to claim 1, wherein the at least one usage limitation parameters is selected from a group consisting of: approval related to usage of a certain range of defined treatment modalities or treatment parameters, approval of accessories used in connection with the defined treatment modalities, and lease/service agreement or access fee related to the biomedical laser.

8. A system for operating a biomedical laser, the biomedical laser having a first range of operational parameters, the system comprising:
a processor coupled to the biomedical laser, the processor being configured to
provide a second range of operational parameters for the biomedical laser, wherein the second range of operational parameters is within the first range of operational parameters;
activate the biomedical laser to operate within the second range of operational parameters;
identify a need for a change in operational parameters of the biomedical laser by detecting a change in geographical location of the biomedical laser and obtaining from a database via a communication network, at least one usage limitation parameter relating to legal regulations governing the operation of the biomedical laser comprising patent restrictions associated with the geographical location of the biomedical laser that may or may not allow use of the biomedical laser; and
trigger an action based on the identified need, wherein the action comprises one of:
providing a third range of operational parameters for the biomedical laser from the database via the communication network, wherein the third range of operation parameters is within the first range of operational parameters; and activating the biomedical laser to operate within the third range of operational parameters; and
de-activating a range of operational parameters.

9. A system according to claim 8, further comprising at least one measuring instrument communicably coupled to the processor, the at least one measuring instrument being configured to measure an operational response of the biomedical laser whilst the biomedical laser is operated using the second range of operational parameters, and wherein the processor is configured to compare the measured operational response with treatment modality parameters of a first treatment to identify the need for the change in operational parameters of the biomedical laser.

10. A system according to claim 8, wherein the processor is configured to compare the treatment modality parameters of the first treatment with the first range of operational parameters to identify the need for the change in operational parameters of the biomedical laser.

11. A system according to claim 8, further comprising a location sensing unit configured to detect a location of the biomedical laser, the location sensing unit being communicably coupled to the processor, wherein the processor is configured to identify the need for the change in operational parameters of the biomedical laser upon detection of change in the location of the biomedical laser.

12. A system according to claim 8, further comprising an identity recognition unit configured to recognizing a user profile of a user using the biomedical laser, the identity recognition unit being communicably coupled to the processor, wherein the processor is configured to identify the need for the change in operational parameters of the biomedical laser upon analysis of the user profile of the user.

13. A system according to claim 8, further comprising an accessory recognition unit configured to obtain information pertaining to accessories used with the biomedical laser, the accessory recognition unit being communicably coupled to the processor, wherein the processor is configured to identify the need for the change in operational parameters of the biomedical laser upon analyzing the obtained information pertaining to the accessories used with the biomedical laser.

14. A system according to claim 8, wherein the at least one usage limitation parameter is selected from a group consisting of: approval related to usage of a certain range of defined treatment modalities or treatment parameters, approval of accessories used in connection with the defined treatment modalities, and lease/service agreement or access fee related to the biomedical laser.

* * * * *